US009686499B2

United States Patent
Ekambaram et al.

(10) Patent No.: US 9,686,499 B2
(45) Date of Patent: Jun. 20, 2017

(54) PHOTO TAGGING WITH BIOMETRIC METADATA GENERATED BY SMART TEXTILES

(71) Applicant: INTERNATIONAL BUSINESS MACHINES CORPORATION, Armonk, NY (US)

(72) Inventors: Vijay Ekambaram, Tamilnadu (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 17 days.

(21) Appl. No.: 14/868,429

(22) Filed: Sep. 29, 2015

(65) Prior Publication Data
US 2017/0094216 A1 Mar. 30, 2017

(51) Int. Cl.
*H04N 5/265* (2006.01)
*H04N 5/907* (2006.01)
*H04N 5/765* (2006.01)
*H04N 5/232* (2006.01)
*G06T 11/60* (2006.01)
*A61B 5/00* (2006.01)

(52) U.S. Cl.
CPC .......... *H04N 5/765* (2013.01); *A61B 5/0077* (2013.01); *G06T 11/60* (2013.01); *H04N 5/23293* (2013.01); *H04N 5/265* (2013.01); *H04N 5/907* (2013.01)

(58) Field of Classification Search
CPC .... H04N 5/765; H04N 5/23293; H04N 5/265; H04N 5/907; A61B 5/0077; G06T 11/60
See application file for complete search history.

(56) References Cited

U.S. PATENT DOCUMENTS

| | | | | |
|---|---|---|---|---|
| 9,285,458 | B2* | 3/2016 | Bajema | G01S 5/02 |
| 2003/0095186 | A1* | 5/2003 | Aman | A63B 24/0021 |
| | | | | 348/162 |
| 2010/0097221 | A1* | 4/2010 | Kreiner | G01S 13/82 |
| | | | | 340/572.1 |
| 2012/0068813 | A1* | 3/2012 | Karttaavi | G01S 13/74 |
| | | | | 340/5.2 |
| 2012/0126973 | A1* | 5/2012 | DeAngelis | A63B 24/0021 |
| | | | | 340/539.13 |

(Continued)

OTHER PUBLICATIONS

Qin, C., Bao, X., Choudhury, R., & Nelakuditi, S. (2012). "TagSense: Leveraging Smartphones for Automatic Image Tagging". IEEE Transactions on Mobile Computing, 13(1), p. 61-74.

*Primary Examiner* — Hung Lam
(74) *Attorney, Agent, or Firm* — Law Office of Jim Boice (57) ABSTRACT

A smart camera includes a photo image capturing device, a biometric data retrieval device, a positioning signal receiver, and a tagging device. The photo image capturing device captures a digitized photograph that shows an image of a person. The biometric data retrieval device requests and receives biometric data for the person from a smart textile garment being worn by the person. The positioning signal receiver receives a positioning signal from a positioning device in the smart textile garment, in order to identify a location of the person within the field of view of the photo image capturing device. The tagging device associates the image of the person with the received biometric data for the person, thereby tagging the image of the person with the biometric data.

18 Claims, 5 Drawing Sheets

(56) References Cited

U.S. PATENT DOCUMENTS

| | | |
|---|---|---|
| 2015/0049946 A1 | 2/2015 | Madineni et al. |
| 2015/0055931 A1 | 2/2015 | Koivukangas et al. |
| 2016/0048722 A1* | 2/2016 | Tayeh ................ G06K 9/00302 382/118 |
| 2016/0210518 A1* | 7/2016 | Script ................ G06K 9/00771 |
| 2016/0337548 A1* | 11/2016 | Osborn .............. H04N 1/32128 |

* cited by examiner

PHOTO TAGGING WITH BIOMETRIC METADATA GENERATED BY SMART TEXTILES

BACKGROUND

The present disclosure relates to the field of smart textiles, and specifically to smart textiles that are used to construct garments. More specifically, the present disclosure relates to using smart textiles to generate biometric metadata that is tagged to a captured image of a person.

SUMMARY

In an embodiment of the present invention, a smart camera includes a photo image capturing device, a biometric data retrieval device, a positioning signal receiver, and a tagging device. The photo image capturing device captures a digitized photograph that shows an image of a person by capturing images within a field of view of the photo image capturing device. The biometric data retrieval device requests and receives biometric data for the person from a smart textile garment worn by the person whose image was captured in the digitized photograph. The positioning signal receiver receives a positioning signal from a positioning device in the smart textile garment worn by the person, in order to identify a location of the person within the field of view of the photo image capturing device. The tagging device associates the image of the person with the received biometric data for the person, thereby identifying a position on the digitized photograph at which the image of the person is located and displaying the biometric data at the position on the digitized image at which the image of the person is located.

In an embodiment of the present invention, a method and/or computer program product tag an image of a person captured in a digitized photograph. A photo image capturing device in a smart camera captures a digitized photograph that includes an image of a person, such that the photo image capturing device captures images within a field of view of the photo image capturing device. A biometric data retrieval device in the smart camera requests and receives biometric data for the person from a smart textile garment worn by the person whose image was captured in the digitized photograph. A positioning signal receiver in the smart camera receives a positioning signal from a positioning device in the smart textile garment worn by the person, such that the positioning signal identifies a location of the person within the field of view of the photo image capturing device. A tagging device in the smart camera tags the image of the person with the received biometric data for the person, such that tagging the image of the person identifies a position on the digitized photograph at which the image of the person is located, and thus tagging the image displays the biometric data at the position on the digitized image at which the image of the person is located.

DETAILED DESCRIPTION

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In one or more embodiments, the present invention is directed to a method of using smart textiles to provide dynamic photo tagging where various contextual information (such as user mood, user dress color, user actions (e.g., walking, running, jumping), humidity, light of the environment, etc.) about every person (wearing smart textiles) depicted in a photograph gets automatically tagged using metadata about the person in the captured digital photo as and when the photo is taken. In a preferred embodiment of the present invention, this dynamic tagging happens in the camera as the photo is being taken, thereby eliminating any offline image processing. Thus, the photo (e.g., digital picture) will have many interesting contextual pieces metadata about the users depicted in the photograph.

Such tagging/metadata provides a novel means for searching photographs. For example, a user may want to see any photographs in which he is wearing a red shirt and blue jeans, or when he was tense, or when the environment was sunny, or when he was running, etc. The metadata described herein, when used to tag the digital photographs, makes such searches feasible.

Being the closest layer to a person's body, textiles provide an ideal platform for the integration of sensors and actuators for physiological signals. Smart textiles (i.e., textiles that combine sensors, actuators and signal processing capabilities) are an important field of application for flexible electronics. Advancement in these fields had led to innovate smart shirts/pants where sensors are integrated with these fabrics, but where the sensors and other electronics are not visible (since they are interwoven into the fabric).

Since a smart textile is always touching the body skin, it can collect a lot of information about a person's physiology, such as their blood pressure, heart rate, body temperature, mood, etc.

Figure 1:
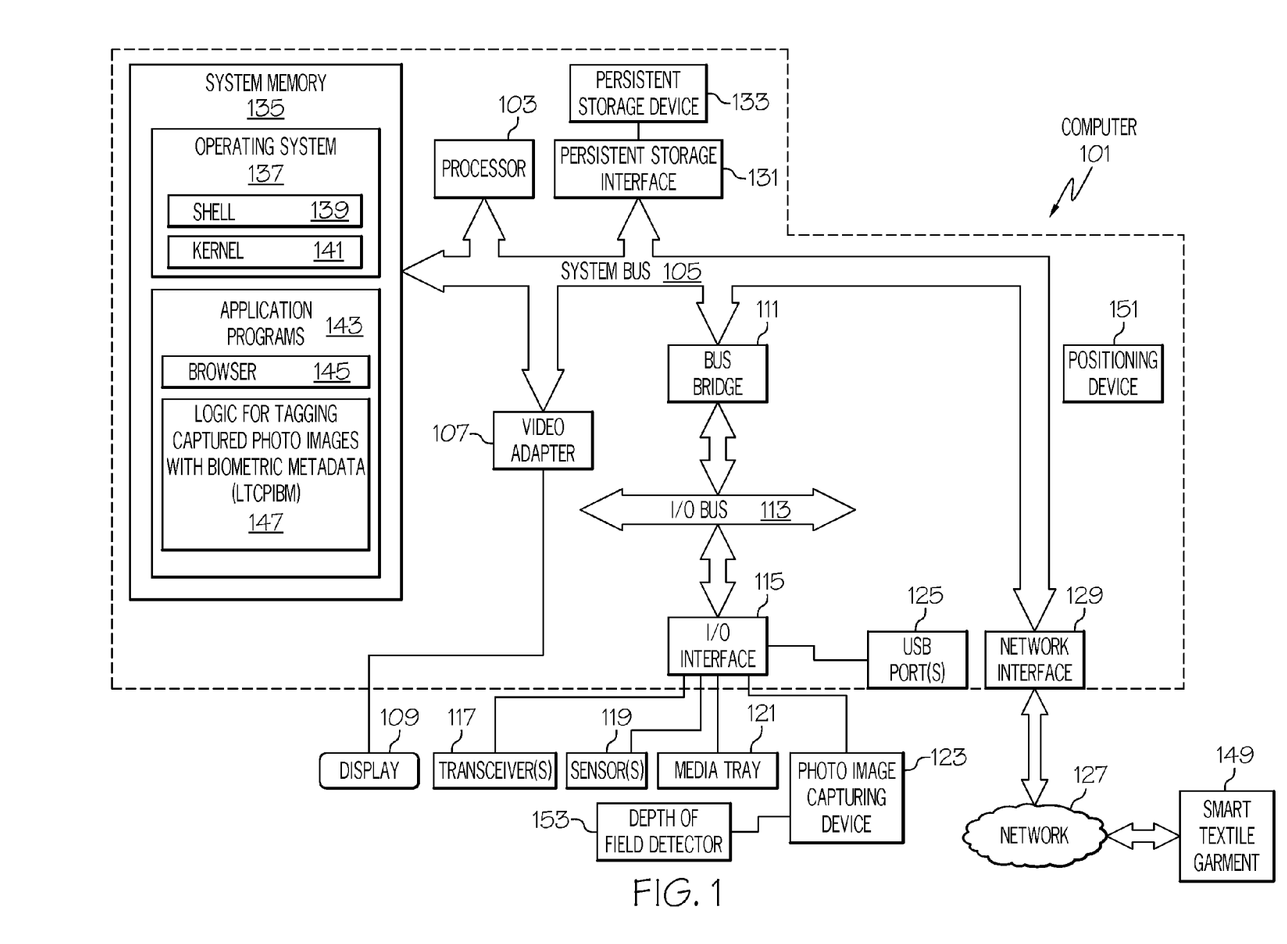
FIG. 1 depicts an exemplary system and network in which the present disclosure may be implemented.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by smart textile garment 149 shown in FIG. 1, and/or smart textile garment 202 shown in FIG. 2, and/or camera 301 introduced in FIG. 3.

Exemplary computer 101 includes a processor 103 that is coupled to a system bus 105. Processor 103 may utilize one or more processors, each of which has one or more processor cores. A video adapter 107, which drives/supports a display 109, is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including transceiver(s) 117, sensor(s) 119, a media tray 121 (which may include storage devices such as CD-ROM drives, multi-media interfaces, etc.), a photo image capturing device 123, and external USB port(s) 125. While the format of the ports connected to I/O interface 115 may be any known to those skilled in the art of computer architecture, in one embodiment some or all of these ports are universal serial bus (USB) ports.

Sensor(s) 119 may be environmental sensors (e.g., light sensors, microphones, chemical detectors, etc.) or biometric sensors (e.g., electroencephalograph (EEG) sensors, electrocardiograph (ECG) sensors, blood pressure sensors, respiration sensors, oxygen saturation sensors, body temperature sensors, etc.), all of which are implemented as electronic devices using technology known to those skilled in the art of environmental/biometric sensors.

Photo image capturing device 123 is a combination of an optical lens (i.e., a physical light focusing lens), a digital lens (i.e., software that is able to focus images on an image capturing medium), and an image capturing medium (e.g., a charge-coupled device (CCD) sensor or a complementary metal-oxide-semiconductor (CMOS) sensor that is able to capture light images that are focused by the optical lens). When combined with computer 101, photo image capturing device 123 is a digital camera (still and/or video), which may be a standalone smart camera, or a component of a mobile phone, computer, etc.

The depth of field detector 153 is a device that is able to determine the depth of field (i.e., the distance between the nearest and farthest objects in a scene that are in focus) of the photo image capturing device 123. This can be determined by sensing the position of the optical lens from the image capturing medium in the photo image capturing device 123, which determines the depth of field of the "camera" (particularly where the optical lens is a fixed lens).

Figure 2:
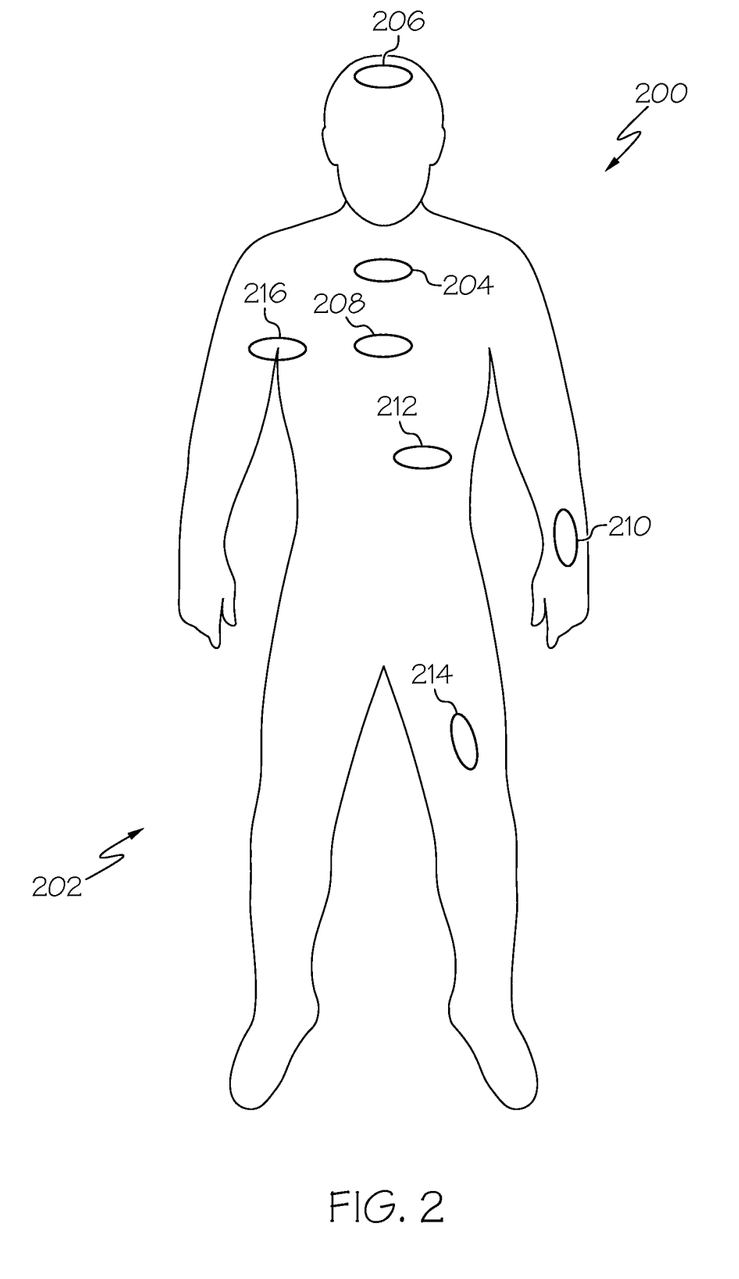
FIG. 2 illustrates a user wearing a smart textile garment in accordance with one or more embodiments of the present invention.
Figure 3:
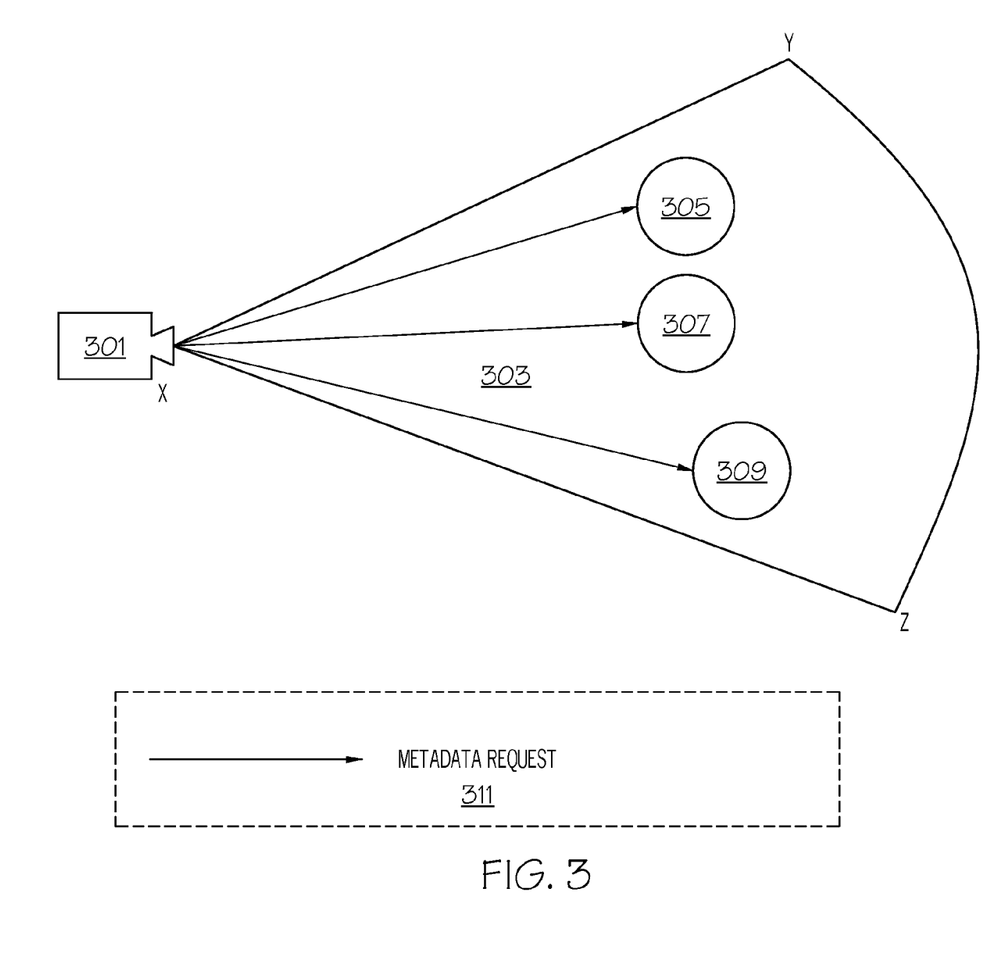
FIG. 3 depicts a smart camera requesting biometric metadata from smart textile garments being worn by persons whose image is captured by the smart camera.

The positioning device 151 is any type of device that is able to determine the physical location of computer 101 (including the smart fabric garment 200 shown in FIG. 2 when the positioning device 151 is incorporated into the smart fabric garment 200), particularly with regard to the relative position of a smart textile garment (e.g., smart textile garment 200 shown in FIG. 2) and a smart camera (e.g., smart camera 301 shown in FIG. 3). Positioning device 151 may use accelerometers, compasses, global positioning system (GPS) detectors, radio frequency transceivers that use signal Doppler shifts in electromagnetic signals between the positioning device 151 and another device, etc.

As depicted, computer 101 is able to communicate with monitoring system 123 using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A persistent storage interface 131 is also coupled to system bus 105. Persistent storage interface 131 interfaces with a persistent storage device 133, such as a hard drive, a static memory, a flash drive, etc. In one embodiment, persistent storage device 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, persistent storage management, and input/output management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication between computer 101 and smart textile garment 149 and/or other systems/devices.

Application programs 143 in computer 101's system memory also include Logic for Tagging Captured Photo Images with Biometric Metadata (LTCPIBM) 147. LTCPIBM 147 includes code for implementing the processes described below, including those described in FIGS. 2-5.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

With reference now to FIG. 2, a user 200 is depicted wearing a smart textile garment 202 in accordance with one or more embodiments of the present invention.

Embedded within smart textile garment 202 are various sensors and associated processing, transmission, and other logic (e.g., components depicted in FIG. 1). Embedded within smart textile garment 202 is an environmental sensor 204 as well as biometric sensors.

Examples of environmental sensor 204 include, but are not limited to, a light sensor (for detecting the light and color of clothing worn by the user as well as ambient/environmental light surrounding the user), a microphone (for detecting sounds made externally and/or internally by the wearer of the smart textile garment 202 as well as ambient sounds around the user), an ambient temperature sensor (i.e., a thermometer that measures the air/water temperature around the user), etc.

Examples of biometric sensors (e.g., sensor(s) 119 shown in FIG. 1) embedded within the smart textile garment 202 include the depicted electroencephalograph (EEG) sensor 206 that measures the brain waves of user 200; a respiration sensor 208 that detects chest movement and/or respiration sounds to detect the respiration rate and quality (e.g., clear or unhealthy) of the breathing of the user 200; a blood pressure sensor 210 (e.g., an electronic blood pressure cuff worn on the wrist); an electrocardiograph (ECG/EKG) sensor 212 that measures heart activity in the user 200; a leg muscle sensor 214, which detects muscle movement and/or ionic electrical activity in the leg muscles to identify leg movement or lack thereof caused by running, walking, sitting, etc.; and/or a sweat sensor 216 (e.g., an ohmmeter that detects a change in skin resistance caused by human sweat).

When used in combination, two or more of the biometric sensors are able to detect an emotional mood of user 200. For example, a combination of readings from the respiration sensor 208, the blood pressure sensor 210, and the sweat sensor 216 is able to determine that the user 200 is calm, anxious, tired, etc.

Thus, the smart textile garment 202 is able to detect the environment around the user 200 and/or biometric states (blood pressure, temperature, mood, etc.) of the user 200.

With reference now to FIG. 3, a camera 301 (using one or more of the components depicted in FIG. 1) it depicted taking a photograph (still or moving) of objects within its field of view 303, including person 305, person 307, and person 309. During the camera click (i.e., when the photo image capture device 123 captures a digital image of person 305, person 307, and person 309), a positioning device (e.g., positioning device 151 shown in FIG. 1) within the camera 301, such as an electronic compass, a GPS device, etc. can identify the direction of capture (i.e., field of view 303). Similarly, the depth of field detector 153 is able to identify the depth of field based on the position of a lens (not shown) on the camera 301 and/or post-processing of the image captured by the camera 301.

One or more of the persons being photographed (e.g., person 305, person 307, and/or person 309) are wearing a smart textile garment, such as the smart textile garment 202 shown in FIG. 2. This allows the smart textile garment(s) to transmit both the location of the wearer as well as environmental/biometric states about the user.

For example, as shown in FIG. 3, when the camera 301 takes the photograph, it simultaneously sends a metadata request 311 to one or more of the persons (person 305, person 307, and person 309) being photographed in the same picture. This metadata request may be for environmental metadata (e.g., the location, temperature, etc. around the person(s) in the photograph) or biometric metadata (e.g., biometric data describing the physiological state of the person(s) themselves). In one or more embodiments of the present invention, this metadata is generated by the smart fabric garment(s) being worn by the persons in the photograph.

Figure 4:
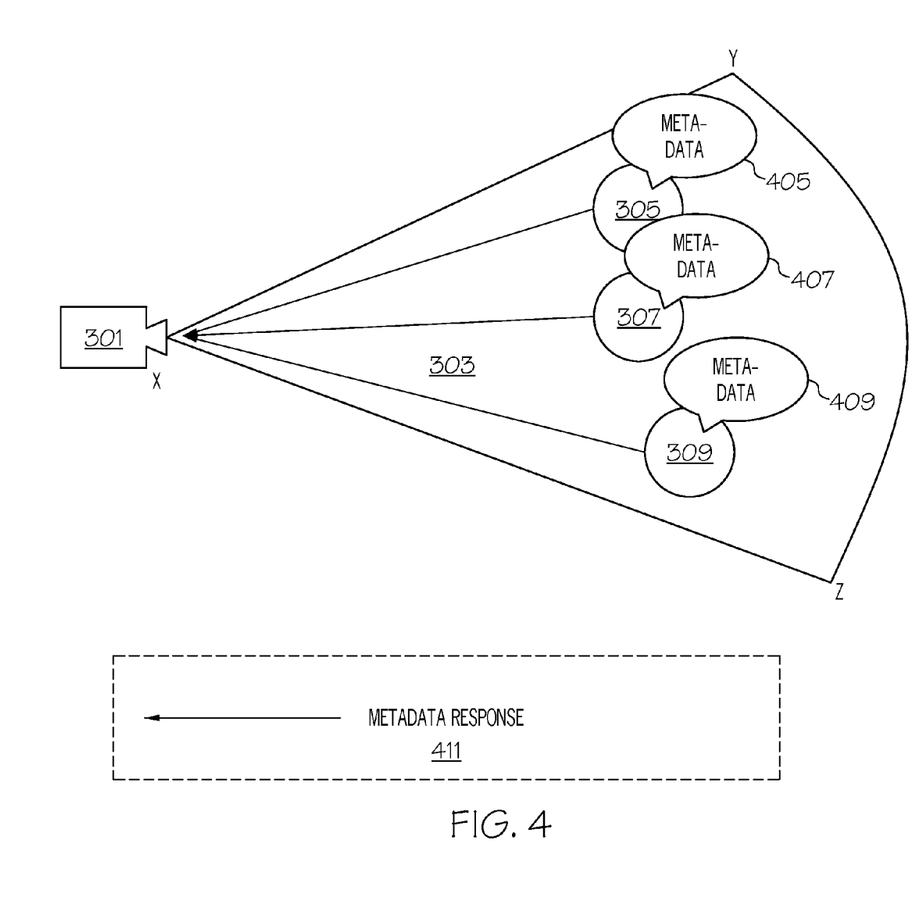
FIG. 4 depicts the smart camera depicted in FIG. 3 receiving the requested biometric metadata from the smart textile garments.

As shown in FIG. 4, when the camera 301 receives a metadata response 411 (which contains the requested metadata from the smart textile garments worn by person 305, person 307, and/or person 309), the camera 301 is able to immediately tag the images of the person 305, person 307, and person 309 with the received metadata (respectively metadata 405, metadata 407, and metadata 409). That is, the digital/digitized photograph captured by the camera 301 of person 305, person 307, and person 309 now has the respective metadata 405/407/409 overlaid on the images of persons 305/307/309 in the photograph.

In one embodiment of the present invention, the captured metadata from the smart textile garment has a unique identifier (e.g., a universally unique identifier—UUID of the person 405) combined with identifiers of the metadata from the smart textile garment (e.g., data that describes the photographed person's mood, clothing, actions (e.g., walking, running, jumping), ambient light, humidity, etc.

When equipped with a positioning device 151 and sensor(s) 119 shown in FIG. 1 (which together are able to identify the field of view 303 of the camera 301 shown in FIG. 3), camera 301 knows the geo-coordinates of each photographed person in its field of view. Since metadata from the smart textile garment may also include the current coordinates from where the metadata was collected, the camera 301 is able to map the persons in the photograph to their associated metadata (generated by the smart textile garment(s) that they are wearing at the time of the photograph).

In another embodiment of the present invention, the camera 301 the images of the persons being photographed with metadata that is generated using facial recognition. That is, facial recognition and analysis software (e.g., part of LTCPIBM 147 shown in FIG. 1) in the camera 301 is able to 1) identify the persons being photographed, and 2) their current mood (e.g., happy, sad, etc.) based on their facial expression(s). As with the biometric sensor metadata described above, these metadata can also get tagged to the persons in the photograph.

Since each photograph is now tagged with metadata generated by the camera 301 and/or the smart textile garment 202 described above, searching and indexing based on this metadata provides a great enhancement to the photo search algorithms. For example, a user may want to retrieve photographs of himself when wearing a red shirt and blue jeans, or when he was tense, or when the day was sunny, or when he was jumping, or when his blood pressure was high, etc. By searching the metadata described herein (which is associated with/tagged to images in digital photographs), the requested types of photographs are easily retrieved.

In one embodiment of the present invention, the system (e.g., computer 101 in FIG. 1) is able to correlate the metadata received from various users in the photograph to create contextual metadata for the entire photograph. For example, by summing the metadata (weighted or un-weighted) for each person's image in the photograph, the overall "mood" or "theme" of the photograph is determined. For example, if most (or even all) of the persons in the photograph are deemed to be happy (based on biometric sensor readings by the smart textile garment 202 and/or the camera 301), then the overall "mood" of the photograph is that of a "happy time". This descriptor can be overlaid as a title on the photograph.

In one embodiment, the present invention utilizes the system described herein for medical purposes. For example, assume that a medical patient is wearing the smart textile garment 202 shown in FIG. 2, and that a camera 301 is taking a photo of the medical patient periodically (e.g., every minute, or else constantly if the photograph is video). If a sensor detects a medical anomaly (e.g., an irregular heart beat), then the metadata developed from readings from the ECG sensor 212 will be displayed on the photograph at a position that is over the patient's heart, thus allowing the health care professional who is monitoring the medical patient to visually recognize what part of the patient's body is having a problem. That is, if the biomedical information developed by the smart textile garment 202 is related to the patient's heart, then this information is displayed on top of the image of the patient at a position on his/her chest where his/her heart is located. Similarly, if the biomedical information developed by the smart textile garment 202 is an EEG reading, then the biomedical information is displayed over the skull/head of patient as depicted in the photographic image.

Thus, when a medical patient is wearing a smart textile garment, sensors in the smart textile garment collect various health related metadata and dynamically stream these metadata to the patient surveillance video capture. The system dynamically overlays all the metadata onto the patient surveillance video, thus giving an excellent user experience for health care providers when checking the status of the medical patient just by looking at the surveillance video.

In one embodiment of the present invention, the metadata tags that are captured also create auto-alarms during critical events. For example, the depicted metadata on the video image of the medical patient may be visually coded to indicate the severity of the medical anomaly being detected. That is, the information generated by the smart textile garment 202 creates metadata about the person depicted in the photographic image (still or video), which is then used to generate alarms and/or recommendations related to that person. These alarms may be warnings of a medical condition (e.g., the patient is having a heart attack), or a recommendation to the health care provider (e.g., recommending that certain medication be administered to alleviate a condition identified by the metadata).

Figure 5:
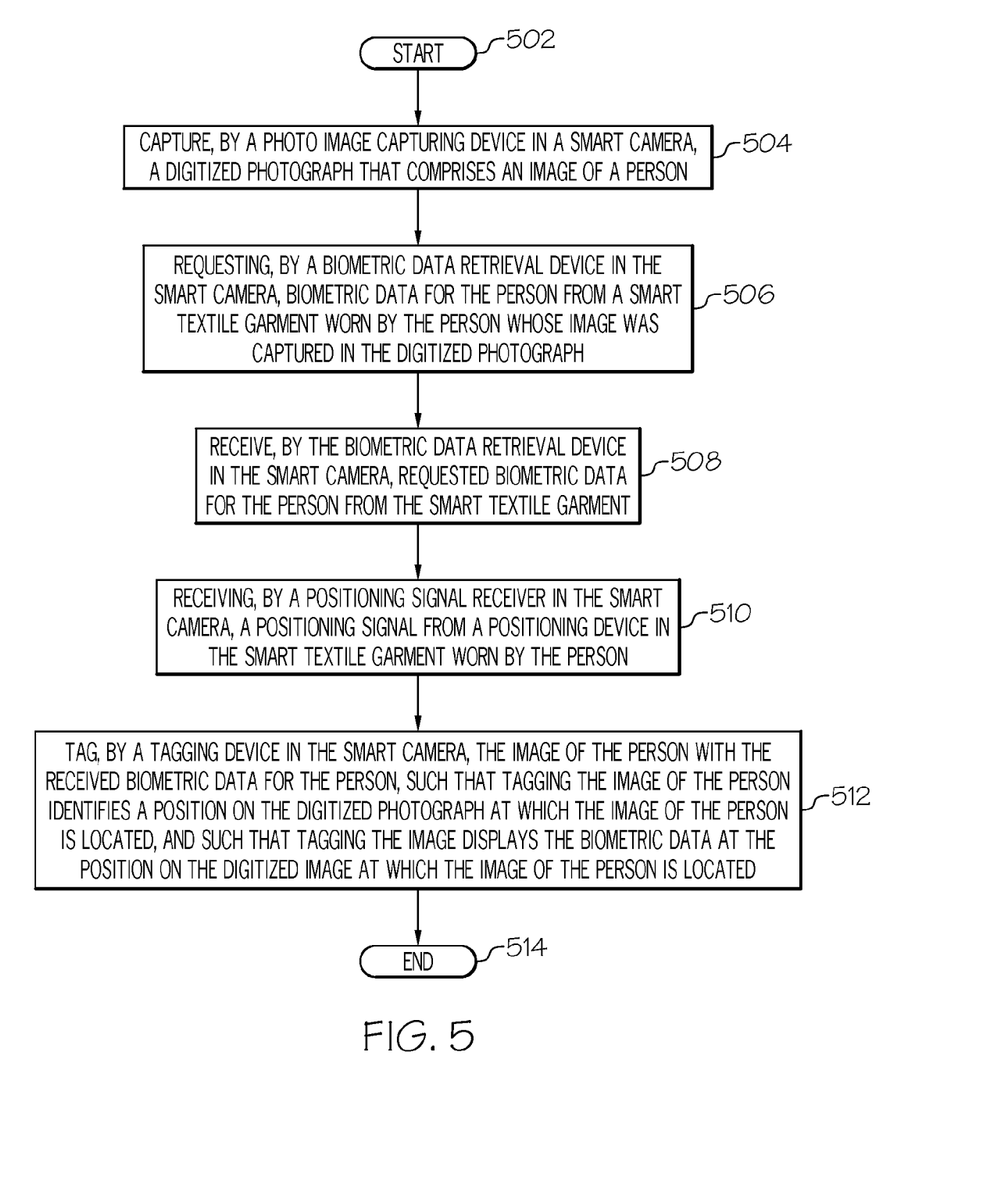
FIG. 5 is a high level flow chart of one or more steps performed by one or more processors and/or other hardware devices to photo tag captured photo images with biometric metadata that is generated by smart textile garments being worn by persons in the photo in accordance with one or more embodiments of the present invention.

With reference now to FIG. 5, a high level flow chart of one or more steps performed by one or more processors and/or other hardware devices to photo tag captured photo images with environmental and/or biometric metadata that is generated by smart textile garments being worn by person in the photo in accordance with one or more embodiments of the present invention is presented.

After initiator block 502, a photo image capturing device in a smart camera captures a digitized photograph, as described in block 504. The digitized photograph includes an image of one or more persons, whose image is captured if they are within a field of view of the photo image capturing device.

As described in block 506, a biometric data retrieval device (e.g., processor 103 in FIG. 1) in the smart camera retrieves biometric data for the person. That is, the biometric data retrieval device retrieves the biometric data about the person that has been generated by the smart textile garment (e.g., smart textile garment 202 shown in FIG. 2) that is being worn by the person(s) whose image(s) were captured in the digitized photograph.

As described in block 508, the biometric data retrieval device in the smart camera receives requested biometric data for the person from the smart textile garment being worn by that person.

As described in block 510, a positioning signal receiver (e.g., transceiver 117 shown in FIG. 1) in the smart camera receives a positioning signal from a positioning device (e.g., positioning device 151 shown in FIG. 1) in the smart textile garment worn by the person. The positioning signal identifies a location of the person within the field of view of the photo image capturing device (i.e., lets the camera 301 know where the person is positioned in the photograph).

As described in block 512, a tagging device (e.g., processor 103) in the smart camera tags the image of the person with the received biometric data for the person. This tagging identifies a position on the digitized photograph at which the image of the person is located (i.e., places a tag over the image of the person in the photograph), and also displays the biometric data at the position on the digitized image at which the image of the person is located (i.e., includes the biometric data about the person in the tag that is overlaid on the image of the person in the photograph).

The flow chart ends at terminator block 514.

In an embodiment of the present invention, a depth of field detector (e.g., depth of field detector 153 shown in FIG. 1) in the smart camera detects the depth of field of the camera as the digitized photograph was captured. The depth of field detector is thus able to identify a particular person based on that particular person being within the depth of field of the smart camera as the digitized photograph was captured. That is, any person within the depth of field of the camera when the photograph was taken is selected to have biometric and/or environmental data from the smart textile garment being worn by that person sent to the camera that is taking his/her picture.

In an embodiment of the present invention, each photograph has a unique identifier. This unique identifier is then associated with the biometric data for the persons in the photograph. For example, one photograph may have a unique identifier of "AAA", and biometric data may be "happy". Thus, by associating "AAA" with "happy" to create the tuple "AAA-happy", then the photograph "AAA" will be located when searching for photographs that are tagged with the biometric data "happy". Therefore, the smart camera generates a unique identifier for each of multiple digitized photographs captured by the smart camera, and then associates biometric data for persons in each of the multiple digitized photographs with the unique identifier of each of the multiple digitized photographs captured by the smart camera, and stores the digitized photographs with the tags locally or remotely. In response to receiving a request for any digitized photograph that is tagged with the biometric data, the smart camera generates an instruction to transmit the digitized photograph that is tagged with the biometric data. This instruction may be transmitted to a server that stores and serves the digitized photographs, or it may be transmitted internally to logic within the camera (assuming that the camera contains the digitized photographs).

In an embodiment of the present invention, the overall "mood" of the photograph is based on biometric readings of multiple persons in the photograph, which allows a user to search for photographs having this overall "mood". Thus, in a scenario in which a single digitized photograph includes images of multiple persons, the biometric data retrieval device retrieves biometric data for each of the multiple persons from smart textile garments worn by the multiple persons whose images were captured in the digitized photograph. The biometric data retrieval device receives the requested biometric data for the multiple persons from the smart textile garments. The smart camera then combines the received biometric data for the multiple persons into a combined biometric signature, which describes an overall biometric state of the multiple persons (and thus the "mood" of the photograph). The smart camera then tags the digitized photograph with the combined biometric signature, and stores the digitized photograph with the tags locally or remotely. In response to receiving a request for any digitized photograph that is tagged with the physical environmental descriptor, the smart camera generates an instruction to transmit all digitized photographs that are tagged with the combined biometric sensor to the requester.

As described herein, in one embodiment of the present invention the smart camera generates a title that describes the combined biometric signature for the digitized photograph, and then overlays the title over the digitized photograph.

In one embodiment of the present invention, the physical conditions (e.g., weather conditions) during which the photograph was taken further describe the photograph, which is then used to locate photographs taken during certain physical conditions. Thus, in this embodiment the smart camera generates a physical environmental descriptor of a physical environment captured by the digitized photograph (e.g., using sensors in the camera or embedded in the smart textile garment that detect lighting conditions, weather conditions, humidity, etc.). The smart camera tags the digitized photograph with the physical environmental descriptor, and stores the digitized photograph with the tags locally or remotely. In response to receiving the request for any digitized photograph that is tagged with the physical environmental descriptor, generating an instruction to transmit the digitized photograph that is tagged with the physical environmental descriptor to the requester.

In one embodiment of the present invention, the smart camera and/or the smart textile garment is able to detect traits (color, style, etc.) of a garment (either a smart textile garment or a traditional garment having not electronics) being worn by a person in a photograph. This information is tagged to the photograph, allowing a user to retrieve any photograph of himself wearing a certain type of clothing. Thus, the smart camera generates a garment descriptor of a garment being worn by the person whose image was captured in the digitized photograph, tags the digitized photograph with the garment descriptor, and stores the tagged digitized photograph locally or remotely. In response to receiving a request for any digitized photograph that is tagged with the garment descriptor, the smart camera generates an instruction to transmit (locally to the smart camera or remotely to a storage server) the digitized photograph that is tagged with the garment descriptor to the requester.

In one embodiment of the present invention, the smart camera is able to tag the person(s) in the photograph as performing some type of physical activity (e.g., jumping, surfing, running, etc.) using metadata generated by the smart textile garment. This allows the user to search for such photographs using the tagging metadata. Thus, the smart camera generates an activity descriptor of the person whose image was captured in the digitized photograph, tags the digitized photograph with the activity descriptor, and then stores the tagged digitized photograph locally (inside the smart camera) or remotely (at a remote photo file server). In response to receiving a request for any digitized photograph that is tagged with the activity descriptor, the smart camera generates an instruction to transmit (locally within the smart camera or to the remote photo file server server) the digitized photograph that is tagged with the activity descriptor to the requester.

As described herein, in one embodiment the person in the photograph is a medical patient, and the biometric data describes a medical condition of the medical patient.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A smart camera comprising:
   a photo image capturing device, wherein the photo image capturing device captures a digitized photograph that comprises an image of a person, and wherein the photo image capturing device captures images within a field of view of the photo image capturing device, and wherein the digitized photograph comprises images of multiple persons;
   a biometric data retrieval device, wherein the biometric data retrieval device requests and receives biometric data for at least one person from the multiple persons from a smart textile garment worn by the at least one person from the multiple persons whose image was captured in the digitized photograph and wherein the biometric data retrieval device further combines received biometric data for the multiple persons into a combined biometric signature, wherein the combined biometric signature describes an overall biometric state of the multiple persons;
   a positioning signal receiver, wherein the positioning signal receiver receives a positioning signal from a positioning device in the smart textile garment worn by the person, and wherein the positioning signal identifies a location of the person within the field of view of the photo image capturing device;
   a tagging device, wherein the tagging device associates the image of the person with the received biometric data for the person, wherein the tagging device identifies a position on the digitized photograph at which the image of the person is located, and wherein the tagging device displays the biometric data at the position on the digitized photograph at which the image of the person is located and wherein the tagging device further tags the digitized photograph with the combined biometric signature;
   wherein the smart camera receives a request from a requester for any digitized photograph that is tagged with the combined biometric signature; and
   wherein the smart camera, in response to receiving the request for any digitized photograph that is tagged with the combined biometric signature, generates an instruction to transmit all digitized photographs that are tagged with the combined biometric signature to the requester.

2. The smart camera of claim 1, further comprising:
   a depth of field detector, wherein the depth of field detector detects a depth of field of the camera as the digitized photograph was captured, and wherein the depth of field detector identifies the person based on the person being within the depth of field of the smart camera as the digitized photograph was captured.

3. A method for tagging an image of a person captured in a digitized photograph, the method comprising:
capturing, by a photo image capturing device in a smart camera, a digitized photograph that comprises an image of a person, wherein the photo image capturing device captures images within a field of view of the photo image capturing device, and wherein the digitized photograph comprises images of multiple persons;
requesting, by a biometric data retrieval device in the smart camera, biometric data for the person from a smart textile garment worn by the person whose image was captured in the digitized photograph;
receiving, by the biometric data retrieval device in the smart camera, requested biometric data for the person from the smart textile garment;
receiving, by a positioning signal receiver in the smart camera, a positioning signal from a positioning device in the smart textile garment worn by the person, wherein the positioning signal identifies a location of the person within the field of view of the photo image capturing device;
tagging, by a tagging device in the smart camera, the image of the person with the received biometric data for the person, wherein tagging the image of the person identifies a position on the digitized photograph at which the image of the person is located, and wherein tagging the image displays the biometric data at the position on the digitized image at which the image of the person is located;
requesting, by the biometric data retrieval device, biometric data for each of the multiple persons from smart textile garments worn by the multiple persons whose images were captured in the digitized photograph;
receiving, by the biometric data retrieval device, requested biometric data for the multiple persons from the smart textile garments;
combining, by the smart camera, received biometric data for the multiple persons into a combined biometric signature, wherein the combined biometric signature describes an overall biometric state of the multiple persons;
tagging, by the smart camera, the digitized photograph with the combined biometric signature;
receiving, by the smart camera, a request from a requester for any digitized photograph that is tagged with the combined biometric signature; and
in response to receiving the request for any digitized photograph that is tagged with the combined biometric signature, generating an instruction to transmit all digitized photographs that are tagged with the combined biometric signature to the requester.

4. The method of claim 3, further comprising:
detecting, by a depth of field detector in the smart camera, a depth of field of the smart camera as the digitized photograph was captured; and
identifying, by the depth of field detector, the person based on the person being within the depth of field of the smart camera as the digitized photograph was captured.

5. The method of claim 3, further comprising:
generating, by the smart camera, a unique identifier for each of multiple digitized photographs captured by the smart camera;

associating, by the smart camera, biometric data for persons in each of the multiple digitized photographs with the unique identifier of each of multiple digitized photographs captured by the smart camera;
receiving, by the smart camera, a request from a requester for any digitized photograph that is tagged with the biometric data; and
in response to receiving the request for any digitized photograph that is tagged with the biometric data, generating, by the smart camera, an instruction to transmit the digitized photograph that is tagged with the biometric data.

6. The method of claim 3, further comprising:
generating, by the smart camera, a title that describes the combined biometric signature for the digitized photograph; and
overlaying, by the smart camera, the title over the digitized photograph.

7. The method of claim 3, further comprising:
generating, by the smart camera, a physical environmental descriptor of a physical environment captured by the digitized photograph;
tagging, by the smart camera, the digitized photograph with the physical environmental descriptor;
receiving, by the smart camera, a request from a requester for any digitized photograph that is tagged with the physical environmental descriptor; and
in response to receiving the request for any digitized photograph that is tagged with the physical environmental descriptor, generating an instruction to transmit the digitized photograph that is tagged with the physical environmental descriptor to the requester.

8. The method of claim 3, further comprising:
generating, by the smart camera, a garment descriptor of a garment being worn by the person whose image was captured in the digitized photograph;
tagging, by the smart camera, the digitized photograph with the garment descriptor;
receiving, by the smart camera, a request from a requester for any digitized photograph that is tagged with the garment descriptor; and
in response to receiving the request for any digitized photograph that is tagged with the garment descriptor, generating an instruction to transmit the digitized photograph that is tagged with the garment descriptor to the requester.

9. The method of claim 3, further comprising:
generating, by the smart camera, an activity descriptor of the person whose image was captured in the digitized photograph;
tagging, by the smart camera, the digitized photograph with the activity descriptor;
receiving, by the smart camera, a request from a requester for any digitized photograph that is tagged with the activity descriptor; and
in response to receiving the request for any digitized photograph that is tagged with the activity descriptor, generating an instruction to transmit the digitized photograph that is tagged with the activity descriptor to the requester.

10. The method of claim 3, wherein the person is a medical patient, and wherein the biometric data describes a medical condition of the medical patient.

11. A computer program product for tagging an image of a person captured in a digitized photograph, the computer program product comprising a non-transitory computer readable storage medium having program code embodied therewith, the program code readable and executable by a processor to perform a method comprising:

capturing, by a photo image capturing device in a smart camera, a digitized photograph that comprises an image of a person, wherein the photo image capturing device captures images within a field of view of the photo image capturing device, and wherein the digitized photograph comprises images of multiple persons;

requesting, by a biometric data retrieval device in the smart camera, biometric data for the person from a smart textile garment worn by the person whose image was captured in the digitized photograph;

receiving, by the biometric data retrieval device in the smart camera, requested biometric data for the person from the smart textile garment;

receiving, by a positioning signal receiver in the smart camera, a positioning signal from a positioning device in the smart textile garment worn by the person, wherein the positioning signal identifies a location of the person within the field of view of the photo image capturing device;

tagging, by a tagging device in the smart camera, the image of the person with received biometric data for the person, wherein tagging the image of the person identifies a position on the digitized photograph at which the image of the person is located, and wherein tagging the image displays the biometric data at the position on the digitized image at which the image of the person is located;

requesting, by the biometric data retrieval device, biometric data for each of the multiple persons from smart textile garments that are worn by the multiple persons whose images were captured in the digitized photograph;

receiving, by the biometric data retrieval device, requested biometric data for the multiple persons from the smart textile garments;

combining, by the smart camera, received biometric data for the multiple persons into a combined biometric signature, wherein the combined biometric signature describes an overall biometric state of the multiple persons;

tagging, by the smart camera, the digitized photograph with the combined biometric signature;

receiving, by the smart camera, a request from a requester for any digitized photograph that is tagged with the combined biometric signature; and in response to receiving the request for any digitized photograph that is tagged with the combined biometric signature, generating an instruction to transmit all digitized photographs that are tagged with the combined biometric signature to the requester.

12. The computer program product of claim 11, wherein the method further comprises:

detecting, by a depth of field detector in the smart camera, a depth of field of the camera as the digitized photograph was captured; and identifying, by the depth of field detector, the person based on the person being within the depth of field of the smart camera as the digitized photograph was captured.

13. The computer program product of claim 11, wherein the method further comprises:

generating, by the smart camera, a unique identifier for each of multiple digitized photographs captured by the smart camera;

associating, by the smart camera, biometric data for persons in each of the multiple digitized photographs with the unique identifier of each of multiple digitized photographs captured by the smart camera;

receiving, by the smart camera, a request from a requester for any digitized photograph that is tagged with the biometric data; and in response to receiving the request for any digitized photograph that is tagged with the biometric data, generating an instruction to transmit the digitized photograph that is tagged with the biometric data.

14. The computer program product of claim 11, wherein the method further comprises:

generating, by the smart camera, a title that describes the combined biometric signature for the digitized photograph; and overlaying, by the smart camera, the title over the digitized photograph.

15. The computer program product of claim 11, wherein the method further comprises:

generating, by the smart camera, a physical environmental descriptor of a physical environment captured by the digitized photograph;

tagging, by the smart camera, the digitized photograph with the physical environmental descriptor;

receiving, by the smart camera, a request from a requester for any digitized photograph that is tagged with the physical environmental descriptor; and in response to receiving the request for any digitized photograph that is tagged with the physical environmental descriptor, generating an instruction to transmit the digitized photograph that is tagged with the physical environmental descriptor to the requester.

16. The computer program product of claim 11, wherein the method further comprises:

generating, by the smart camera, a garment descriptor of a garment being worn by the person whose image was captured in the digitized photograph;

tagging, by the smart camera, the digitized photograph with the garment descriptor;

receiving, by the smart camera, a request from a requester for any digitized photograph that is tagged with the garment descriptor; and in response to receiving the request for any digitized photograph that is tagged with the garment descriptor, generating an instruction to transmit the digitized photograph that is tagged with the garment descriptor to the requester.

17. The computer program product of claim 11, wherein the method further comprises:

generating, by the smart camera, an activity descriptor of the person whose image was captured in the digitized photograph;

tagging, by the smart camera, the digitized photograph with the activity descriptor;

receiving, by the smart camera, a request from a requester for any digitized photograph that is tagged with the activity descriptor; and in response to receiving the request for any digitized photograph that is tagged with the activity descriptor, generating an instruction to transmit the digitized photograph that is tagged with the activity descriptor to the requester.

18. The computer program product of claim 11, wherein the person is a medical patient, and wherein the biometric data describes a medical condition of the medical patient.

* * * * *